(12) United States Patent
Meneghini et al.

(10) Patent No.: US 7,879,043 B2
(45) Date of Patent: Feb. 1, 2011

(54) SYSTEM AND METHOD FOR PREVENTING INTRAOPERATIVE FRACTURE IN CEMENTLESS HIP ARTHROPLASTY

(75) Inventors: Robert Michael Meneghini, 3328 Kilkenny Cir., Carmel, IN (US) 46032; Phillip John Cornwell, 4007 N. Bob White St., Terre Haute, IN (US) 47805; Aaron Glen Rosenberg, 200 Oakmont Dr., Deerfield, IL (US) 60015

(73) Assignees: Robert Michael Meneghini, Carmel, IN (US); Phillip John Cornwell, Terre Haute, IN (US); Aaron Glen Rosenberg, Deerfield, IL (US)

( * ) Notice: Subject to any disclaimer, the term of this patent is extended or adjusted under 35 U.S.C. 154(b) by 727 days.

(21) Appl. No.: 11/604,873

(22) Filed: Nov. 28, 2006

(65) Prior Publication Data

US 2008/0125671 A1 May 29, 2008

(51) Int. Cl.
| | |
|---|---|
| A61B 17/58 | (2006.01) |
| A61B 17/60 | (2006.01) |
| A61B 19/00 | (2006.01) |
| A61B 5/103 | (2006.01) |
| A61B 5/117 | (2006.01) |
| A61F 2/00 | (2006.01) |

(52) U.S. Cl. .................. 606/99; 600/553; 600/587; 606/102

(58) Field of Classification Search .................. 600/553, 600/587, 595; 606/86 R, 89, 99, 102, 130
See application file for complete search history.

(56) References Cited

U.S. PATENT DOCUMENTS

| | | | |
|---|---|---|---|
| 4,437,473 A | 3/1984 | Mollan | |
| 4,754,763 A | 7/1988 | Doemland | |
| 4,799,498 A | 1/1989 | Collier | |
| 4,819,753 A | 4/1989 | Higo et al. | |
| 4,836,218 A | 6/1989 | Gay et al. | |

(Continued)

FOREIGN PATENT DOCUMENTS

JP 10-211174 A 8/1998

(Continued)

OTHER PUBLICATIONS

Ilizaliturri et al., Victor. "Small Incision Total Hip Replacement by the Lateral Approach Using Standard Instruments." *Ortho Blue Journal*. vol. 27. No. 4. (Apr. 2004):pp. 377-381.

(Continued)

*Primary Examiner*—Max Hindenburg
*Assistant Examiner*—Adam J Eiseman
(74) *Attorney, Agent, or Firm*—Posz Law Group, PLC

(57) ABSTRACT

A method and system for monitoring impaction of a femoral component of a hip prosthesis into a femur in which impaction data generated during the impaction of the femoral component into the femur is received from at least one measurement transducer attached to the femoral component and is normalized by a data acquisition and analysis device. An impaction monitoring metric is calculated based on the normalized impaction data, and femoral component fit and stability data is then generated and output to a user interface based on the impaction monitoring metric.

13 Claims, 4 Drawing Sheets

U.S. PATENT DOCUMENTS

| | | | |
|---|---|---|---|
| 4,986,281 | A | 1/1991 | Preves et al. |
| 5,024,239 | A | 6/1991 | Rosenstein |
| 5,368,044 | A | 11/1994 | Cain et al. |
| 5,518,008 | A * | 5/1996 | Cucchiaro et al. ............ 600/590 |
| 5,836,876 | A | 11/1998 | Dimarogonas |
| 5,836,891 | A | 11/1998 | Dimarogonas |
| 5,897,494 | A | 4/1999 | Flock et al. |
| 6,245,109 | B1 | 6/2001 | Mendes et al. |
| 7,001,393 | B2 | 2/2006 | Schwenke et al. |
| 7,097,662 | B2 | 8/2006 | Evans, III et al. |
| 2002/0143268 | A1 | 10/2002 | Meredith et al. |
| 2004/0106916 | A1* | 6/2004 | Quaid et al. .................... 606/1 |
| 2005/0101962 | A1* | 5/2005 | Schwenke et al. ............. 606/86 |
| 2006/0217640 | A1 | 9/2006 | Trandafir |
| 2007/0149981 | A1 | 6/2007 | Bhattacharyya |

FOREIGN PATENT DOCUMENTS

| | | |
|---|---|---|
| JP | 11-169352 A | 6/1999 |

OTHER PUBLICATIONS

Jasty et al., Murali. "High Assembly Strains and Femoral Fractures Produced During Insertion of Uncemented Femoral Components: A Cadaver Study." *The Journal of Arthroplasty*. vol. 8. No. 5 (1993):pp. 479-487.

Zhou et al., X.M. "Effect of Press-fit Femoral Stems on Strains in the Femur: A Photoelastic Coating Study." *The Journal of Arthroplasty*. vol. 5. No. 1 (Mar. 1990): pp. 71-82.

Aamodt et al., A. "Changes in Proximal Femoral Strain After Insertion of Uncemented Standard and Customised Femoral Stems: An Experimental Study in Human Femora." *The Journal of Bone & Joint Surgery (Br)*. vol. 83. No. 6. (Aug. 2001):pp. 921-929.

Elias et al., John. "Medial Cortex Strain Distribution During Noncemented Total Hip Arthroplasty." *Clinical Orthopaedics and Related Research*. No. 370 (2000):pp. 250-258.

Herzwurm et al., Paul. "Prophylactic Cerclage: A Method of Preventing Femur Fracture in Uncemented Total Hip Arthroplasty." *Eisenhower Army Medical Center*. vol. 15. No. 2 (Feb. 1992):pp. 143-146.

Berry et al., Daniel. "Symposium: Minimally Invasive Total Hip Arthroplasty: Development, Early Results, and a Critical Analysis." *The Journal of Bone & Joint Surgery: The Orthopaedic Forum*. vol. 85-A. No. 11 (Nov. 2003):pp. 2235-2246.

Berger, Richard A. "Total Hip Arthroplasty Using Minimally Invasive Two-Incision Approach." *Clinical Orthopaedics and Related Research*. No. 417 (2003):pp. 232-241.

Berger et al., Richard A. "Rapid Rehabilitation and Recovery with Minimally Invasive Total Hip Arthroplasty." *Clinical Orthopaedics and Related Research*. No. 429 (2004):pp. 239-247.

Berger, Richard A. "Mini-Incision Total Hip Replacement using an Anterolateral Approach: Technique and Results." *Orthopaedic Clinics of North America*. vol. 35 (2004):pp. 143-151.

DiGioia et al., Anthony M. "Mini-Incision Technique for Total Hip Arthoplasty with Navigation." *The Journal of Arthroplasty*. vol. 18. No. 2 (Feb. 2003):pp. 123-128.

Hartzband et al., Mark A. "Posterolateral Minimal Incision for Total Hip Replacement: Technique and Early Results." *Orthopaedic Clinics of North America*. vol. 35 (2004):pp. 119-129.

Kennon et al., Robert E. "Total Hip Arthroplasty Through a Minimally Invasive Anterior Surgical Approach." *The Journal of Bone & Joint Surgery*. vol. 85-A. Supp. 4 (2003):pp. 39-48.

Sculco, Thomas. "Minimally Invasive Total Hip Arthoplasty: In the Affirmative." *The Journal of Arthroplasty*. vol. 19. No. 4. Supp. 1 (Jun. 2004):pp. 78-80.

Wenz et al., James. "Mini-Incision Total Hip Arthroplasty: A Comparative Assessment of Perioperative Outcomes." *Ortho Blue Journal*. vol. 25. No. 10 (2002): pp. 1031-1043.

Arcibeck et al., Michael J. "Learning Curve for the Two-Incision Total Hip Replacement." *Clinical Orthopaedics and Related Research*. No. 429 (2004):pp. 232-238.

Jasty et al., Murali. "In Vivo Skeletal Responses to Porous-Surfaced Implants Subjected to Small Induced Motions." *The Journal of Bone & Joint Surgery*. vol. 79-A. No. 5 (May 1997):pp. 707-714.

Falez et al., Francesco. "Intraoperative Type I Proximal Femoral Fractures: Influence on the Stability of Hydroxyapatite-Coated Femoral Components." *The Journal of Arthroplasty*. vol. 13. No. 6 (Sep. 1998):pp. 653-659.

Jasty et al., Murali. "Unrecognized Femoral Fractures During Cementless Total Hip Arthroplasty in the Dog and their Effect on Bone Ingrowth." *The Journal of Arthroplasty*. vol. 7. No. 4 (Dec. 1992):pp. 501-508.

Heiner et al., Anneliese. "Structural Properties of a New Design of Composite Replicate Femurs and Tibias." *Journal of Biomechanics*. vol. 34 (2001):pp. 773-781.

Kurtz et al., Steven. "Prevalence of Primary and Revision Total Hip and Knee Arthroplasty in the United States From 1990 Through 2002." *The Journal of Bone & Joint Surgery*. vol. 87-A. No. 7 (Jul. 2005):pp. 1487-1497.

Schwartz et al., JT. "Femoral Fracture During Non-cemented Total Hip Arthroplasty." *The Journal of Bone & Joint Surgery*. vol. 71-A. No. 8 (Sep. 1989):pp. 1135-1142.

Hjorth, Bo. "Technical Contributions: EEG Analysis Based on Time Domain Properties." *Electroencephalography and Clinical Neurophysiology*. vol. 29 (1970):pp. 306-310.

M. M. Reda Taha et al. "Introduction to Use of Wavelet Multiresolution Analysis for Intelligent Structural Health Monitoring." *NRC*. (2004): 719-731.

David O. Smallwood. "Characterization and Simulation of Transient Vibrations Using Band Limited Temporal Moments." *Shock and Vibration*. vol. 1 No. 6. (1994): 507-527.

Thomas A. Butler et al. "Model Validation for a Complex Jointed Structure." *Los Alamos National Laboratory*. 1318-1324.

A. N. Robertson et al. "Singularity Detection for Structural Health Monitoring Using Holder Exponents." *Los Alamos National Laboratory*. (2003): 1163-1184.

Seana Giardini et al. Monitoring Femoral Component Insertion in Cementless Total Hip Arthroplasty. *Los Alamos National Laboratory*.

Anneliese D. Heiner et al. "Structural Properties of a New Design of Composite Replicate Femurs and Tibias." *Journal of Biomechanics*. (2001): 773-781.

Seana Giardini. "Exploration of Damage Identification Techniques to Determine Placement of Femoral Component During Total Hip Arthroplasty." i-74.

Deena Abou-Trabi et al. Monitoring Femoral Component Insertion During Uncemented Total Hip Arthroplasty.

B. F. Feeny et al. "A Decrament Method for the Simultaneous Estimation of Coulomb and Viscous Friction." *Journal of Sound and Vibration*. (1996): 149-154.

T. Kijewski et al. "Wavelet Transforms for System Identification in Civil Engineering." *Computer-Aided Civil and Infrastructure Engineering*. (2003):339-355.

M. Ruzzene et al. "Natural Frequencies and Dampings Identification Using Wavelet Transform: Application to Real Data." *Mechanical Systems and Signal Processing*. (1997): 207-218.

J. Slavič et al. "Damping Identification Using a Continuous Wavelet Trasnform: Application to Real Data." *Journal of Sound and Vibration*. (2003): 291-307.

Norden E. Huang et al. "The Empirical Mode Decomposition and the Hilbert Spectrum for Nonlinear and Non-stationary Time Series Analysis." *The Royal Society*. (1996): 903-995.

Norden E. Huang et al. "A Confidence Limit for the Empirical Mode Decomposition and Hibert Spectral Analysis." *The Royal Society*. (2003): 2317-2345.

Timothy J. Johnson et al. "Transmissibility as a Differential Indicator of Structural Damage." *ASME*. (2002): 634-641.

Crisman et al., *Femoral Component Insertion Monitoring Using Human Cadaveric Specimens*, IMAC, Jan. 2007.

Giardini et al., *Monitoring Femoral Component Insertion in Cementless Total Hip Arthroplasty*, IMAC, Jan. 2005.

Abou-Trabi et al., *Monitoring Femoral Component Insertion in Uncemented Total Hip Arthroplasty*, IMAC, Jan. 2006.

Giardini et al., *Monitoring Femoral Component Installation Using Vibration Testing*, Rocky Mountain Bioengineering Symposium & International ISA Biomedical Sciences Instrumentation Symposium, Apr. 8, 2005, pp. 13-18.

Slavičc et al., *Damping Identification Using a Continuous Wavelet Transform: Application to Real Data*, Journal of Sound and Vibration 262, 2003, 291-307.

Huang et al., *The Empirical Mode Decomposition and the Hilbert Spectrum for Nonlinear and Non-stationary Time Series Analysis*, The Royal Society, Nov. 4, 1996, pp. 903-995.

Huang et al., *A Confidence Limit for the Empirical Mode Decomposition and Hibert Spectral Analysis*, The Royal Society, Jul. 23, 2003, pp. 2317-2345.

Reda Taha et al., *Introduction to Use of Wavelet Multiresolution Analysis for Intelligent Structural Health Monitoring*, NRC, Oct. 1, 2004, pp. 719-731.

Smallwood, *Characterization and Simulation of Transient Vibrations Using Band Limited Temporal Moments*, Shock and Vibration, vol. 1 No. 6., Feb. 17, 1994, pp. 507-527.

Butler et al., *Model Validation for a Complex Jointed Structure*, Los Alamos National Laboratory, pp. 1318-1324.

Robertson et al., *Singularity Detection for Structural Health Monitoring Using Holder Exponents*, Los Alamos National Laboratory, Sep. 9, 2002, pp. 1163-1184.

Heiner et al., *Structural Properties of a New Design of Composite Replicate Femurs and Tibias*, Journal of Biomechanics. Jan. 10, 2001, pp. 773-781.

Giardini., *Exploration of Damage Identification Techniques to Determine Placement of Femoral Component During Total Hip Arthroplasty*, Eli Lily/Guidant Applied Life Sciences Research Center at Rose-Hulman Institute of Technology, Apr. 29, 2005 pp. i-74.

Johnson et al., *Transmissibility as a Differential Indicator of Structural Damage*, ASME, vol. 124, Oct. 2002, pp. 634-641.

Feeny et al., *A Decrament Method for the Simultaneous Estimation of Coulomb and Viscous Friction*, Journal of Sound and Vibration, Nov. 17, 1995, pp. 149-154.

Kijewski et al., *Wavelet Transforms for System Identification in Civil Engineering*, Computer-Aided Civil and infrastructure Engineering, 2003, pp. 339-355.

Ruzzene et al., *Natural Frequencies and Dampings Identification Using Wavelet Transform: Application to Real Data*, Mechanical Systems and Signal Processing, Oct. 1997, pp. 207-218.

R. Puers, et al., "A telemetry system for the detection of hip prosthesis loosening by vibration analysis," www.sciencedirect.com, Sensors and Actuators A: Physical, vol. 85, Issues 1-3, Aug. 25, 2000, pp. 42-47 (abstract enclosed).

\* cited by examiner

| SIGNAL PROCESSING TECHNIQUES APPLICABLE TO IMPACTION DATA |
|---|
| CHARACTERISTICS |
| FREQUENCY |
| DOMINANT FREQUENCY VIA CONTINUOUS WAVELET TRANSFORM |
| ENERGY IN HIGH VS. LOW FREQUENCY BANDS |
| MEAN FREQUENCY OF HIGHEST RMS INTRINSIC MODE FUNCTION |
| MEAN SQUARE VALUE OF SIGNAL IN FREQUENCY BAND |
| MEAN OF CROSS POWER SPECTRAL DENSITY BETWEEN SUBSEQUENT HITS |
| VARIANCE OF CROSS POWER SPECTRAL DENSITY BETWEEN SUBSEQUENT HITS |
| STATIC STIFFNESS VIA THE FRFs FROM ACCELERATIONS |
| TIME HISTORY |
| NORM OF ACCELERATION/NORM OF FORCE |
| MOBILITY |
| MAX. TRANSVERSE ACCELERATION/MAX. Z-DIRECTION ACCELERATION |
| INVERSE OF COMPLEXITY |
| SIGNAL STATIONARITY |
| SIGNAL STATIONARITY VIA HILBERT HUANG TRANSFORM |
| INTERRELATION |
| AREA UNDER COHERENCE FUNCTION BETWEEN SUBSEQUENT HITS |
| TRANSMISSIBILITY BETWEEN TRANSVERSE ACCELEROMETERS |
| MAXIMUM CROSS CORRELATION |
| NEURAL NETWORK |
| ARTIFICAL NEURAL NETWORK TRAINED WITH WAVELET DECOMPOSED SIGNAL |
| ENERGY DISSIPATION |
| TIME TO 99% OF TOTAL NORM |
| DECAY OF HIGHEST RMS INTRINSIC MODE FUNCTION VIA HILBERT TRANSFORM |
| CHANGES IN SYSTEM PARAMETERS VIA FRFs |
| DAMPING ESTIMATE VIA CONTINUOUS WAVELET TRANSFORM |
| COULOMB AND VISCOUS DAMPING OF FILTERED SIGNAL |

*FIG. 6*

SYSTEM AND METHOD FOR PREVENTING INTRAOPERATIVE FRACTURE IN CEMENTLESS HIP ARTHROPLASTY

BACKGROUND

The present invention relates generally to human joint replacement surgery, and particularly to a method and system that enable an orthopedic surgeon to monitor impaction data, such as vibration data, generated during impaction of the femoral component of a hip prosthesis into a femur and determine maximal femoral component interference fit and prosthetic stability to prevent femoral fractures during the impaction process.

Total hip replacement, or hip arthroplasty, is one of the most consistently successful surgical procedures in medicine. Recently, new minimally invasive surgical techniques in hip arthroplasty that offer numerous advantages over standard surgical approaches have been introduced. These purported advantages include shorter hospital stays, more rapid rehabilitation and recovery, less blood loss, and diminished postoperative pain.

However, there are some potential drawbacks to minimally invasive surgical techniques. Although such techniques require smaller incisions compared to conventional techniques, the smaller incisions diminish the surgeon's ability to adequately visualize the entire proximal femur. This decrease in visual ability places additional emphasis on the surgeon's auditory and tactile senses in determining the optimal interference fit, or seating, of the implant within the geometry of the proximal femur, which is required for maximal implant stability.

With emerging minimally invasive surgical techniques in total hip arthroplasty, there is anecdotal evidence of an increase in periprosthetic fractures associated with insertion of the femoral component. This is likely the result of diminished visibility, auditory and tactile feedback for the surgeon operating through smaller incisions. Intraoperative periprosthetic femur fractures may occur if the implant is impacted past the point of maximal interference fit, subjecting the cortical bone of the proximal femur to excessive hoop stresses. Such fractures, especially if unrecognized, decrease the mechanical stability of the femoral component and may increase the risk of implant failure that is likely a result of diminished early bone ingrowth from fracture-induced instability and micromotion.

SUMMARY

The present invention provides a method and system for supplementing the surgeon's tactile and auditory senses by using damage identification techniques based on vibration characteristics associated with femoral component impaction to determine when a femoral component implant is fully seated.

More specifically, a method and system for monitoring impaction of a femoral component of a hip prosthesis into a femur in which impaction data generated during the impaction of the femoral component into the femur is received from at least one measurement transducer, such as a piezoelectric transducer (PZT) and/or an accelerometer, attached to the femoral component and is normalized by a data acquisition and analysis device. An impaction monitoring metric is calculated based on the normalized impaction data, and femoral component fit and stability data is then generated and output to a user interface based on the impaction monitoring metric.

BRIEF DESCRIPTION OF THE DRAWINGS

The accompanying figures, in which like reference numerals refer to identical or functionally similar elements throughout the separate views and which, together with the detailed description, are incorporated in and form part of the specification, serve to further illustrate various embodiments and to explain various principles and advantages in accordance with the present invention.

FIG. 6 is a table of additional signal processing techniques that may be applied to normalize femoral component impaction data for use in monitoring impaction of a femoral component of a hip prosthesis into a femur in accordance with various exemplary embodiments.

DETAILED DESCRIPTION

Figure 1:
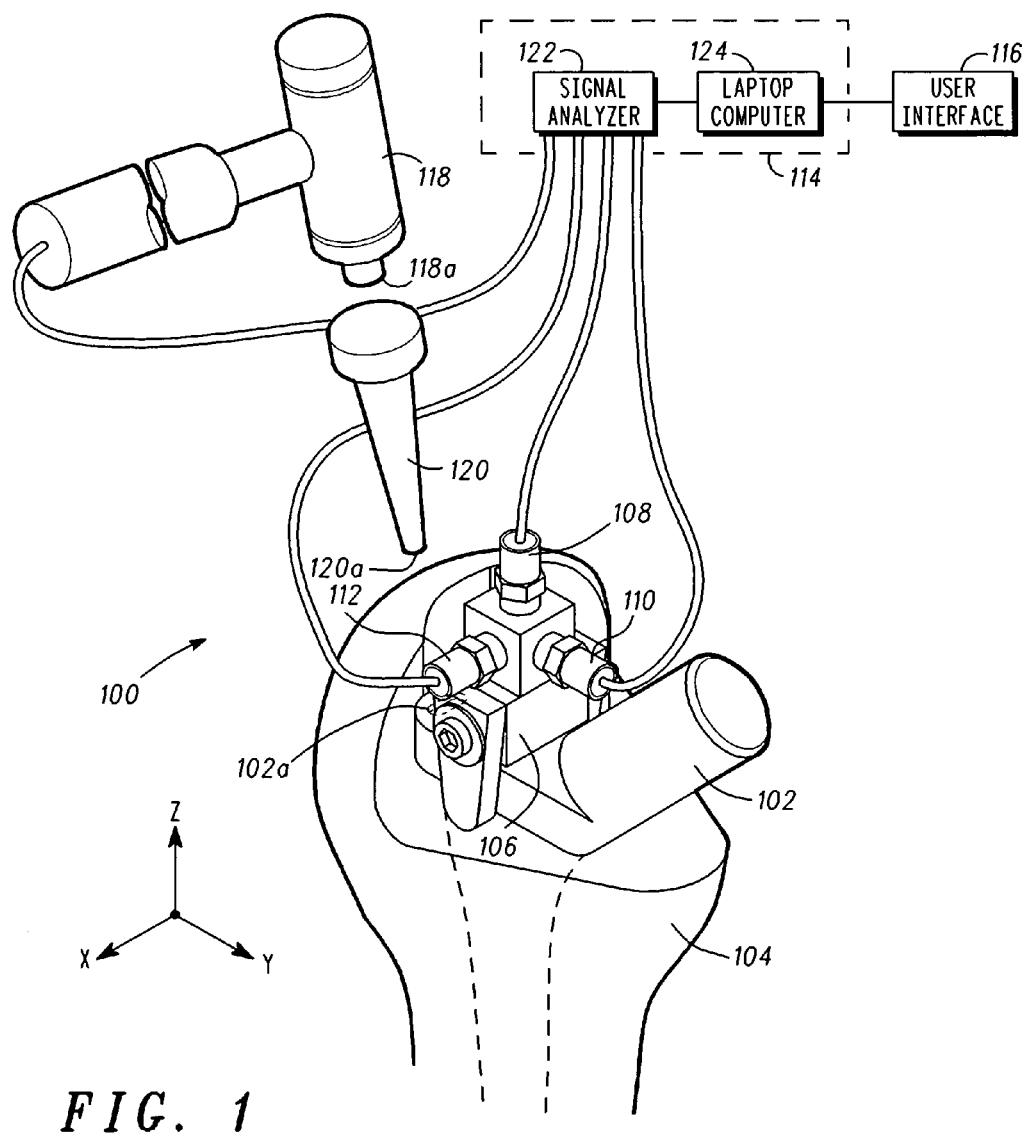
FIG. 1 is a schematic diagram of a system for monitoring femoral component fit and stability during impaction of a femoral component of a hip prosthesis into a femur according to an exemplary embodiment.

Referring now to the drawings in which like reference numbers reference like parts, FIG. 1 shows a system 100 for monitoring femoral component fit and stability during impaction of a tapered cementless femoral component 102 (femoral component) of a hip prosthesis into a femur 104 according to an exemplary embodiment. The femoral component 102 may be made, for example, from a titanium alloy with a porous titanium mesh around the circumference of the proximal half of the stem, such as a FiberMetal Taper component manufactured by Zimmer, Inc. of Warsaw, Ind. The system 100 is designed for use in minimally invasive cementless hip arthroplasty in which the surgeon must determine proper seating of the femoral component 102 with minimal tactile and auditory feedback to avoid intraoperative fractures in the femur caused by overseating of the femoral component. However, the system 100 is also generally applicable to any joint replacement procedure that involves impaction of a prosthetic component into bone and that requires accurate component seating.

The system 100 includes a testing component 106 on which is mounted at least one measurement transducer, such as accelerometers 108, 110 and 112, a data acquisition and analysis device 114 in communication with the measurement transducers 108, 110, 112, and a user interface 116 in communication with the data acquisition and analysis device 114. The structure and operation of each of these system components will be discussed below in detail.

The testing component 106 is preferably a reusable component, such as a 6061 aluminum fixture that may be bolted or otherwise attached to the femoral component 102. However, the term testing component as used throughout the present description refers generally to the component or components used to generate femoral component impaction data. The testing component 106 is configured to function essentially as a mounting block for the accelerometers 108, 110, 112. Each of the accelerometers 108, 110, 112 is operable to detect vibrations resulting from the impaction of the femoral component 102 into the femur 104 and to correspondingly generate detection signals including impaction data.

Specifically, the accelerometer 108 is oriented in an impaction direction of the femoral component along a relative z axis, while the transverse accelerometers 110, 112 are oriented orthogonally to the relative z axis along relative x and y axes, respectively. The accelerometer 108 oriented along the z axis is preferably a shock accelerometer, such as a PCB Piezotronics Model No. 352B01 accelerometer, with a nominal sensitivity of approximately 1 mV/g, a measurement range of approximately 10,000 g and a frequency range of approximately 20 kHz. The accelerometers 110, 112 respectively oriented along the x and y axes are each preferably an accelerometer, such as a PCB Piezotronics Model No. 353B13 accelerometer, with a nominal sensitivity of approximately 5 mV/g, a measurement range of approximately 2,000 g and a frequency range of approximately 20 kHz.

The accelerometer 108 is configured to detect the impaction force generated when a hammer, such as the hammer 118, impacts a punch 120. The hammer 118 may be a standard surgeon's hammer or may be instrumented with a force transducer. If implemented with a force transducer, such as Piezotronics Model No. PCB 086C05, with a sensitivity of approximately 1 mV/lbf, a frequency range of approximately 5 kHz and an amplitude range of 5,000 lbf, the hammer 118 is placed in communication with the data acquisition and analysis device 114 as shown in FIG. 1 to enable the data acquisition and analysis device 114 to record input force generated by the hammer 118. The hammer 118 may also be fitted with a hard tip 118a to better simulate a standard surgeon's hammer. The punch 120 may include a bottom end 120a that fits into a slot in the top end 102a of the femoral component 102. The punch 120 may or may not be placed in communication with the data acquisition and analysis device 114 depending upon the particular system set-up.

The data acquisition and analysis device 114 is configured to receive the impaction data from the accelerometers 108, 110, 112, the hammer 118 and/or the punch 120, normalize the impaction data into a usable format as normalized impaction data, calculate an impaction monitoring metric and output femoral component fit and stability data based on the impaction monitoring metric. The data acquisition and analysis device 114 is shown as including a signal analyzer 122, such as an eight channel Dactron Spectrabook Dynamic Signal Analyzer, manufactured by LDS Test and Measurement, LLC, and a laptop computer 124 that runs data acquisition software such as RT Pro software. The computer 124 also executes instructions stored on a computer readable medium, such as a hard drive or CD-ROM, with the instructions including a computer implemented method for monitoring impaction of a femoral component of a hip prosthesis into a femur, such as the method that will be discussed below in connection with the flow diagram 200 in FIG. 2.

The user interface 116 is configured to receive the femoral component fit and stability data output from the data acquisition and analysis device and provide feedback indicative of the femoral component fit and stability data to the surgeon. The user interface 116 may be a computer display or any other visual, audio or audiovisual device capable of providing to the surgeon feedback that is indicative of the femoral component fit and stability data and that is generated in a manner that will now be discussed.

Figure 2:
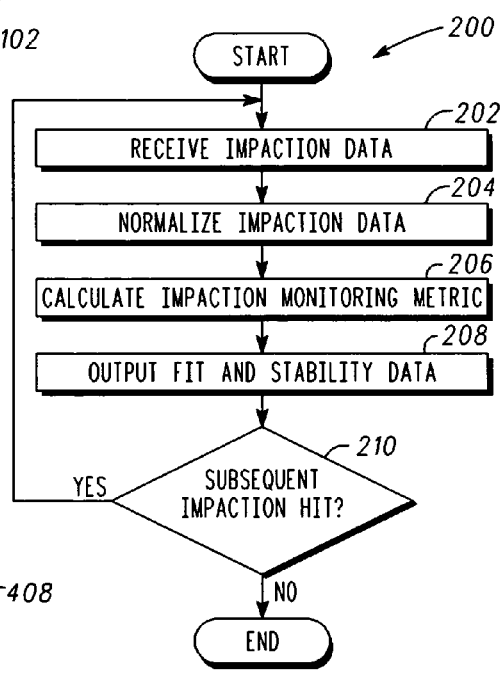
FIG. 2 is a flow diagram illustrating an exemplary method for monitoring impaction of a femoral component of a hip prosthesis into a femur.

Turning now to FIG. 2, a method of monitoring impaction of the femoral component 102 by the system 100 in FIG. 1 will now be discussed in connection with the flow diagram 200. At 202, the data acquisition and analysis device 114 receives impaction data generated during the impaction of the femoral component 102 into the femur 104 from at least one of the accelerometers 108, 110, 112 attached to the femoral component 102 by way of the testing component 106. According to one exemplary embodiment, it has been determined experimentally that the z-axis acceleration most closely corresponds to the seating of the femoral component. Therefore, use of the data from the accelerometer 108 will be assumed for purposes of the present description.

At 204, when the data acquisition and analysis device 114 receives the impaction data, such as impact force data from the accelerometer 108 and acceleration data from the accelerometers 110, 112, the data acquisition and analysis device 114 normalizes the impaction data into a usable format as normalized impaction data. According to the presently discussed exemplary embodiment, impaction data is normalized to remove the effect of the magnitude of the input signal.

At 206, the data acquisition and analysis device 114 calculates an impaction monitoring metric indicative of the time that it takes a measured impaction signal to obtain a fraction, or percentage, of its total norm. This metric is associated with an increase in signal damping that occurs as the femoral component 102 nears a fully seated position in the femur 104. Such a technique is advantageous in that input data from the hammer 118 and/or the punch 120 is not required.

More specifically, the data acquisition and analysis device 114 is programmed to calculate a total norm of an acceleration signal including the impaction data as shown in Eq. 1:

$$Norm_{Total} = \sqrt{\sum_{i=1}^{N} a_i^2} \qquad (Eq. 1)$$

where N is a number of points in a time interval to be analyzed and a is an acceleration measurement taken at an $i^{th}$ point by the accelerometer 108. Once $Norm_{total}$ is calculated as in Eq. 1, the data acquisition and analysis device calculates the impaction monitoring metric as a fraction of the total norm of the impaction signal during the time interval at a $j^{th}$ point as shown in Eq. 2:

$$E_j = \frac{\sqrt{\sum_{i=1}^{j} a_i^2}}{Norm_{Total}} \qquad (Eq. 2)$$

where a time t(j) corresponding to a fractional value $E_j$ within a predetermined range indicative of the femoral component being fully seated is determined for each of a plurality of femoral component impaction hits. Based on experimental evidence, it has been determined that a time $t_j$ corresponding to a value $E_j$=0.99 provides an accurate indication of when the femoral component 102 is fully seated. The data acquisition and analysis device 114 first filters any linear trends associated with the acceleration data prior to calculating $E_j$ using Eq. 2. At 208, the data acquisition and analysis device 114 then outputs femoral component fit and stability data based on the calculated impaction monitoring metric to the user interface 116 to enable the surgeon to determine whether the femoral component 102 is fully seated. At 210, the data acquisition and analysis device 114 monitors for a subsequent impaction hit. If no such hit is detected, the method ends. If another impaction hit is detected, the method returns to 202 and is repeated.

Figure 3A:
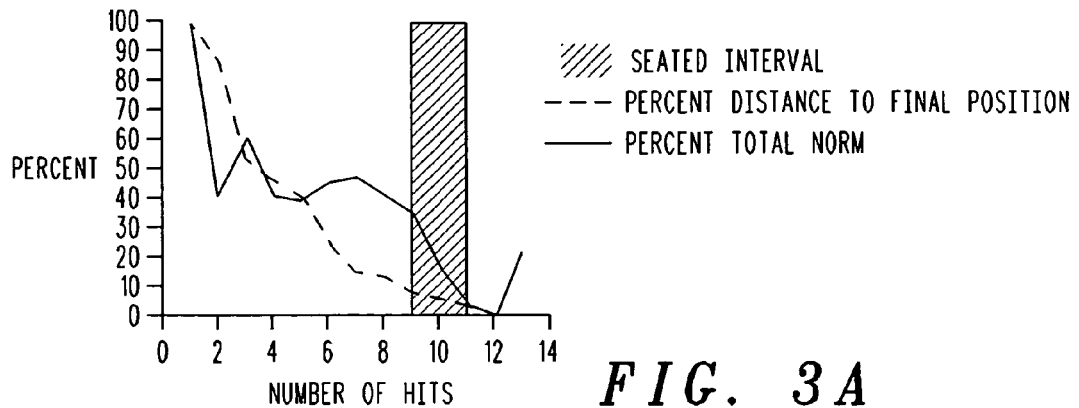
FIGS. 3A-3C are graphs of experimental data illustrating the relationship between percentage distance to final seated position of the femoral component and the percentage to total normalized metric within a seated interval based on data generated by the system shown in FIG. 1.
Figure 3B:
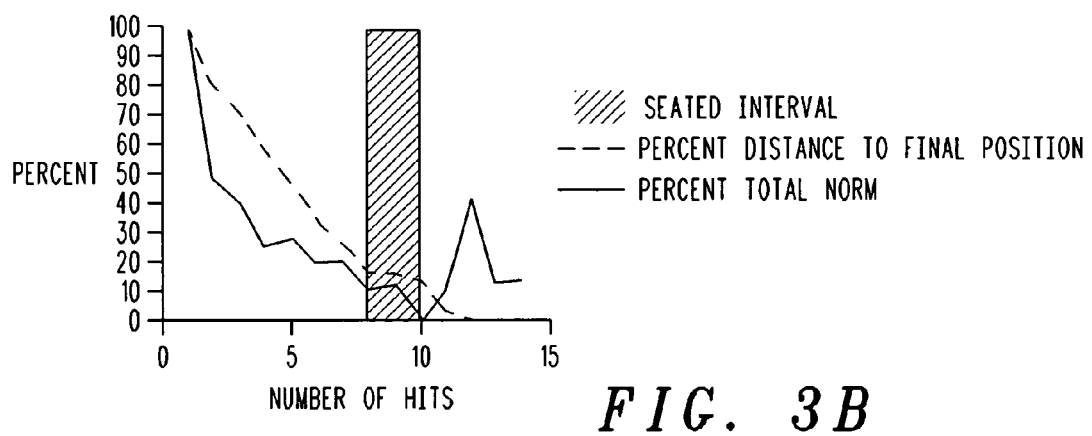
Figure 3C:
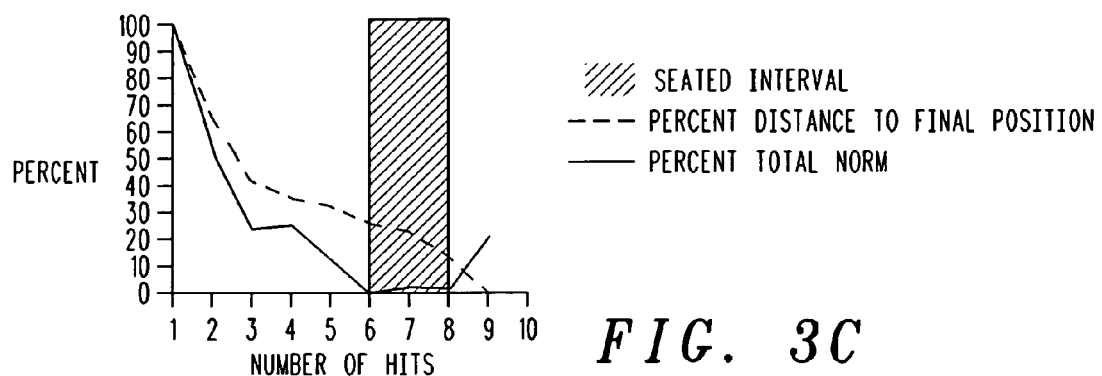

FIGS. 3A, 3B and 3C graphically illustrate experimental femoral component impaction results for three separate cementless hip arthroplasty procedures as expressed by percent distance to final seated position versus number of impaction hits. As shown, the shaded area represents a range of hits in which the femoral component is considered to be seated, factoring in the somewhat subjective nature of when different surgeons would consider the femoral component to be seated. The dotted lines in each graph represent the actual percentage of distance of the femoral component to its final seated position as measured from the top of the prosthesis to the opening of the femoral canal, while the solid lines in each graph represent the percentage of the total norm of an impaction signal as calculated in Eq. 2 above. As shown in FIGS. 3A-3C, calculation of the 99% to norm metric represents an accurate method of determining when the femoral component is seated.

The above data was generated under the following experimental conditions. Cadaveric specimens were used, with each one being placed in the lateral decubitus position. A standard anterolateral approach to the hip was utilized to expose and dislocate the hip, as it occurs during total hip arthroplasty. Dislocation was performed after an anterior capsulotomy and was achieved with hip flexion, adduction and external rotation. The operative leg was then positioned over the contralateral extremity to adequately expose the proximal femur. Radiographic evaluation was unavailable prior to the procedure. Therefore, the femoral neck osteotomy and femoral preparation were performed without the benefit of preoperatively assessing the femoral size, canal shape, anatomy identification, and overall bone quality.

The femoral neck osteotomy was made approximately one finger-width above the lesser trochanter, which was visualized directly. The removed femoral neck was sent to a laboratory for further analysis of bone quality including bone mineral density (BMD). A box osteotome was used to enter the proximal femur and ensure adequate removal of the lateral femoral neck. The T-handled Charnley awl was then used by hand to establish intramedullary access and alignment. Reamers were not used during any portion of the femoral preparation.

Broaching of the femur was then performed utilizing broaches of increasing sizes until appropriate axial and rotational stability was obtained as determined by the performing surgeon. The broaches were always inserted in an orientation that approximated the femoral neck anteversion. Once the final broach was determined, the identical sized femoral implant was selected.

The surgeon placed the implant, with accelerometers attached to a testing component as shown for example in FIG. 1, into the proximal femur and pressed it in as far as possible by hand. A depth measurement was then taken using calipers from the most superior aspect of the femoral trunnion to the most medial aspect of the medial femoral calcar at the location of the osteotomy. The implant was then impacted once with hammer and punch, during which acceleration response was recorded. The distance was measured and recorded immediately after each impaction and the progression and degree of component seating into the proximal femur was documented. The surgeon, based on his experience and by failure of the implant to advance visibly into the femur with consecutive impacts, stated when the implant was seated. This point was noted and then the femoral component was impacted further with the intention of creating a periprosthetic fracture.

In certain cases, progressive seating of the implant occurred well below the level of the medial neck osteotomy and failed to produce a fracture. The lack of fracture likely indicated an implant undersized relative to the femoral anatomy. In the remaining cases, progressive seating occurred followed by periprosthetic fracture of the femur. This fracture point was also noted. After the data were collected it was exported to MATLAB and analyzed.

Figure 5:
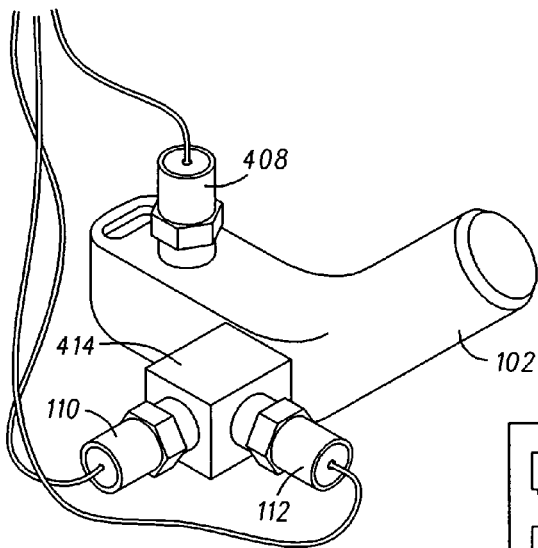
FIG. 5 is a perspective view showing in more detail the components in FIG. 4 as attached to the femoral component of the hip prosthesis.
Figure 4:
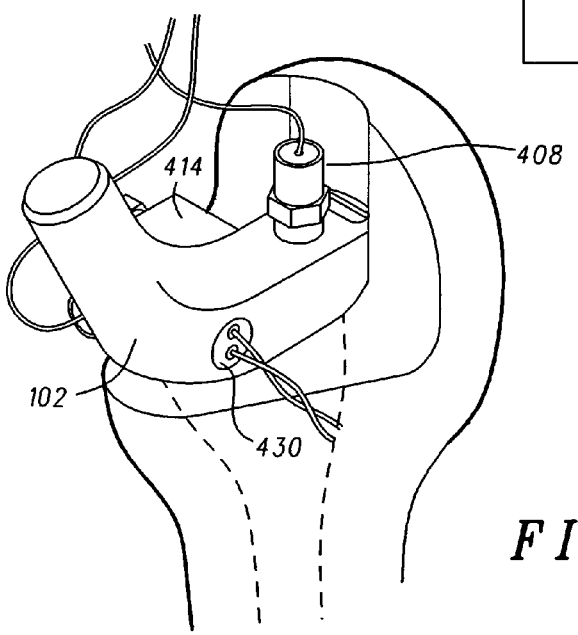
FIG. 4 is a perspective view showing measurement transducers as attached to a femoral component of a hip prosthesis in accordance with yet another exemplary embodiment.

Referring now to FIGS. 4 and 5, the femoral component is shown at 102. However, unlike FIG. 1, one or more impaction measurement transducers, such as a z-axis accelerometer 408 oriented along an impaction direction on a relative z axis and a piezoelectric transducer (PZT) patch 430, are directly attached to the femoral component 102 rather than to an instrumented testing component, while transverse accelerometers 110, 112 are mounted on, for example, a block 414 that is attached to the femoral component 102. In such an embodiment, the z-axis accelerometer 408 and the PZT patch 430 may be considered the testing component if utilized without the transverse accelerometers 110, 112. The PZT patch 430 may be, for example, a 0.25 inch diameter model APC 850 patch attached by, for example, an adhesive resin cement such as M-Bond.

Prior to impaction, a femoral component impedance measurement may be taken through the PZT patch 430, which is in communication with the data acquisition and analysis device 116 of FIG. 1, and frequency response functions (FRFs) between the PZT patch 430 and the accelerometers 408, 110, 112 may be determined using the data acquisition and analysis device 116. A band-limited Gaussian white excitation may then be input through the PZT patch 430 between hits, sampled at a rate of, for example, 200 kHz and the FRFs then averaged a predetermined number of times to eliminate noise. A Hanning window may be applied to the data to minimize leakage.

Specifically, after the above preliminary measurements, once the femoral component is placed into the femur, the impedance and FRF measurements may be repeated and used as baselines for subsequent measurements. During impact of the femoral component, acceleration time history data may be acquired from the accelerometers 408, 110, 112 and the force transducer on the hammer 118 may be used to acquire the force input. A predetermined number of data samples may be taken without a window at a sampling rate of, for example, 40 kHz. The data acquisition is triggered using the force input to obtain 10 pre-data points. Therefore, as the force crosses a predetermined threshold, the data acquisition and analysis device 114 may acquire force signals as well as 10 samples prior to impaction, thereby enabling signals to be acquired in their entirety.

The data acquisition and analysis device 114 may be programmed with software to calculate representative FRFs from one of the accelerometers 408, 110, 112 based on the excitation signals generated by the PZT patch 430. It has been noted through experimentation that an impaction monitoring metric calculated between impaction hits based on convergence of resonance signal frequencies and anti-resonance signal frequencies in the 10.5 kHz-12 kHz band or based on peak magnitudes of these frequencies in the 9 kHz-11 kHz band are indicative of whether a femoral component is or is not fully seated.

FIG. 6 is a table of additional processing techniques capable of being used in systems similar to those described above to calculate impaction monitoring metrics. Each of the listed processing techniques may be implemented by programming the above discussed data acquisition and analysis device 114 in a manner that will be understood by one skilled in the art to generate metrics indicative of femoral component seating based on signals received from one or more measurement transducers such as the accelerometers 108, 110, 112 the hammer 118 and/or the punch 120 in FIG. 1 and/or the accelerometer 408 and the PZT patch 430 in FIG. 4. Specifically, as shown, the measurement transducer signals may be processed to produce metrics based on signal frequency, signal time history, signal stationarity, signal interrelation, neural network calculations and/or signals indicative of energy dissipation.

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

What is claimed is:

1. A method for monitoring impaction of a femoral component of a hip prosthesis into a femur, comprising:
   receiving impaction data generated during the impaction of the femoral component into the femur from at least one accelerometer attached to the femoral component;
   normalizing the impaction data into a usable format as normalized impaction data;
   calculating a total norm of an acceleration signal including the normalized impaction data based on the following equation:

$$Norm_{Total} = \sqrt{\sum_{i=1}^{N} a_i^2}$$

where N is a number of points in a time interval to be analyzed and a is an acceleration measurement taken at an $i^{th}$ point by the accelerometer;
   calculating an impaction monitoring metric $E_j$ for a femoral component impaction hit as a fraction of the total norm of the acceleration signal during the time interval at a $j^{th}$ point based on the following equation:

$$E_j = \frac{\sqrt{\sum_{i=1}^{j} a_i^2}}{Norm_{Total}}$$

determining a time t(j) corresponding to a fractional value $E_j$ within a predetermined range indicative of the femoral component being fully seated for each of a plurality of femoral component impaction hits that is equal to a length of time required for $E_j$ to reach a predetermined fractional value indicative of femoral component fit and stability after the impaction hit; and
   generating an output based on the time t(j) for the femoral component impaction hit, the output being indicative of the femoral component fit and stability.

2. The method of claim 1, wherein the length of time t(j) required for $E_j$ to reach a predetermined fractional value indicative of femoral component fit and stability after the impaction hit corresponds to $E_j=0.99$.

3. The method of claim 1, wherein the receiving of impaction data comprises receiving output acceleration data generated during the impaction of the femoral component into the femur from a single accelerometer attached to the femoral component.

4. The method of claim 3, wherein the single accelerometer is oriented in an impaction direction of the femoral component along a relative z axis.

5. The method of claim 1, wherein the generating an output based on the time t(j) for the femoral component impaction hit comprises generating an output based on the time t(j) corresponding to $E_j=0.99$ for the femoral component impaction hit.

6. A system for monitoring femoral component fit and stability during impaction of a femoral component of a hip prosthesis into a femur, comprising:
   a testing component including at least one accelerometer that is attachable to the femoral component, the at least one accelerometer being operable to generate impaction data corresponding to the impaction of the femoral component into the femur;
   a data acquisition and analysis device in communication with the at least one accelerometer and configured to receive the impaction data, normalize the impaction data into a usable format as normalized impaction data and calculate an impaction monitoring metric by calculating
   (1) a total norm of an acceleration signal including the normalized impaction data as $$Norm_{Total} = \sqrt{\sum_{i=1}^{N} a_i^2}$$

where N is a number of points in a time interval to be analyzed and a is an acceleration measurement taken at an $i^{th}$ point by the accelerometer,
   (2) a fraction of the total norm of the acceleration signal during the time interval at $j^{th}$ point as $$E_j = \frac{\sqrt{\sum_{i=1}^{j} a_i^2}}{Norm_{Total}}$$

and
   (3) a time t(j) that is equal to a length of time required for $E_j$ to reach a predetermined fractional value indicative of femoral component fit and stability after each of a plurality of femoral component impaction hits; and
   a user interface in communication with the data acquisition and analysis device and configured to provide feedback indicative of femoral component fit and stability data based on the impaction monitoring metric.

7. The system of claim 6, wherein the length of time required for $E_j$ to reach a predetermined fractional value indicative of femoral component fit and stability is $E_j=0.99$.

8. The system of claim 6, wherein the at least one accelerometer comprises an output accelerometer for generating an output acceleration signal including the impaction data generated by impaction of the femoral component.

9. The system of claim 6, wherein the at least one accelerometer comprises a single accelerometer attached to the femoral component and oriented in an impaction direction of the femoral component along a relative z axis.

10. A system for monitoring femoral component fit and stability during impaction of a femoral component of a hip prosthesis into a femur, comprising:
   a testing component including at least one measurement transducer that is attachable to the femoral component, the at least one measurement transducer being operable to generate impaction data corresponding to the impaction of the femoral component into the femur;
   a data acquisition and analysis device in communication with the at least one measurement transducer and configured to receive the impaction data, normalize the impaction data into a usable format as normalized impaction data, calculate an impaction monitoring metric, and calculate a time $t_{(j)}$ required for the impaction monitoring metric to reach a predetermined value that is indicative of a femoral component fit and stability for each impaction hit; and
   a user interface in communication with the data acquisition and analysis device and configured to provide feedback based on the value of $t_{(j)}$ for each impaction hit;
   wherein the data acquisition and analysis device is configured to calculate the impaction monitoring metric based on the normalized impaction data by processing measurement transducer signals including the impaction data to produce an impaction monitoring metric based on at least one of signal frequency, signal time history, signal stationarity, signal interrelation, neural network calculations and/or energy dissipation.

11. A computer readable medium comprising instructions that are executable by a computer, the instructions including a computer implemented method for monitoring impaction of a femoral component of a hip prosthesis into a femur, the instructions for implementing the steps of:
   receiving impaction data generated during the impaction of the femoral component into the femur from at least one transducer attached to the femoral component; and
   normalizing the impaction data into a usable format as normalized impaction data by calculating a total norm of an acceleration signal including the impaction data as $$Norm_{Total} = \sqrt{\sum_{i=1}^{N} a_i^2}$$

where N is a number of points in a time interval to be analyzed and a is an acceleration measurement taken at an $i^{th}$ point by the accelerometer; and
   calculating a fraction of the total norm of the impaction signal during the time interval at a $j^{th}$ point as an impaction monitoring metric based on the following formula:

$$E_j = \frac{\sqrt{\sum_{i=1}^{j} a_i^2}}{Norm_{Total}}$$

and;
   where a time, t(j), corresponding to a fractional value $E_j$ within a predetermined range indicative of the femoral component being fully seated is determined for calculating a time t(j) that is equal to a length of time required for $E_j$ to reach a predetermined fractional value indicative of femoral component fit and stability after each of a plurality of femoral component impaction hits.

12. The computer readable medium of claim 11, wherein the length of time required for $E_j$ to reach a predetermined fractional value indicative of femoral component fit and stability is 0.99.

13. The computer readable medium of claim 11, wherein the instructions are further for implementing the step of:
   generating an output based on the time t(j) for each of the femoral component impaction hits, the output being indicative of femoral component fit and stability.

* * * * *